United States Patent [19]

Gilden et al.

[11] 4,270,544
[45] Jun. 2, 1981

[54] MEDICAL ELECTRODE HAVING IMPROVED ADHERENCE CHARACTERISTICS

[75] Inventors: Sheldon J. Gilden, Sharon; Robert H. Robichaud, Attleboro, both of Mass.

[73] Assignee: Texas Instruments Incorporated, Attleboro, Mass.

[21] Appl. No.: 40,839

[22] Filed: May 21, 1979

[51] Int. Cl.³ .............................................. A61B 5/04
[52] U.S. Cl. .................................... 128/640; 128/641
[58] Field of Search ............................ 128/639–641, 128/644, 783, 798, 802, 803, 155–157

[56] References Cited

U.S. PATENT DOCUMENTS

| | | | |
|---|---|---|---|
| 1,845,630 | 2/1932 | Scholl | 128/155 X |
| 3,865,099 | 2/1975 | Robichaud | 128/641 |
| 3,991,754 | 11/1976 | Gertzman | 128/156 |
| 4,029,086 | 6/1977 | Corasonti | 128/641 |
| 4,090,752 | 5/1978 | Long | 128/641 X |
| 4,182,346 | 1/1980 | Allison | 128/641 |

FOREIGN PATENT DOCUMENTS 2440836 3/1976 Fed. Rep. of Germany ........... 128/639

Primary Examiner—Lee S. Cohen
Attorney, Agent, or Firm—John A. Haug; Patrick J. McAndrews; Melvin Sharp

[57] ABSTRACT

A medical electrode unit has a dielectric body formed with a cavity therein in which are mounted a sensory electrode accessible from one side of the body, and a foam pad, having a surface adjacent an opposite side of the body. The foam pad is saturated with an electrolyte and adapted to be held on the skin of a patient by means of a flexible piece of material secured to the dielectric body surrounding the cavity and having a layer of pressure sensitive adhesive coated on a surface of the material. Once applied to the skin a fluid column of electrolyte extends from the skin to the sensing electrode. A protective cover is releasably fastened to the adhesive layer and extends over the foam pad until ready for use at which time it is peeled from the flexible piece of material. The flexible piece of material, in the form of a ring of foam is provided with a plurality of slits extending through the material from top to bottom in order to promote ventilation of the skin area covered by the electrode unit. Several different slit configurations are disclosed all of which minimize moisture retention without adversely effecting the forces available for holding the unit to the patient's skin.

8 Claims, 6 Drawing Figures

MEDICAL ELECTRODE HAVING IMPROVED ADHERENCE CHARACTERISTICS

This invention relates generally to medical electrodes and more particularly to electrode units adapted to be adhered to a patient's skin.

Medical electrode units which are prefilled with electrolyte gel or paste for permitting the electrode unit to be speedily and conveniently mounted on a patient's skin to enable certain physiological monitoring of the patient are well known. Such electrode units are the subject matter of U.S. Pat. No. 3,865,099, assigned to the assignee of the present invention. In these prefilled electrodes, a conductive electrode sensing element is disposed within a cavity in a dielectric body so that when the unit is mounted on a patient's skin the sensing element is held in spaced relation to the skin. A foam pad filled with electrolyte gel is disposed in the cavity for retaining the electrolyte in position between the sensing element and the open end of the cavity. A ring of flexible material having a surface with a pressure sensitive adhesive layer thereon is attached to and projects from the body to permit attachment of this unit to a patient's skin. When use of this unit is required, a protective cover is removed from the unit, the dielectric body is secured to the patient's skin by means of the adhesive ring, with the electrolyte gel forming a fluid column between the patient's skin and the sensing electrode element. A lead from an electrocardiograph or other physiological measuring apparatus is secured to the sensing electrode element for receiving signals from the patient's skin as will be understood.

Although in some situations it may be desirable for such electrode units to be attached to a patient's skin for only a short duration of time, for example a matter of a few minutes, in other instances it may be necessary or desirable to monitor physiological activity of a patient over a protracted period of time. In such situations if the skin of the patient, to which unit is being adhered, has been improperly prepared, or if a particular patient has a propensity for heavy perspiration or for some other reason, the units unknowingly become loose on the patient's skin—spurious electrical signals may be produced as a result thereof. Thus in order to obviate this problem it is desirable to provide a unit which will adhere to a patient's skin for a predetermined minimum time period, for example five days, and if such patient monitoring is to be extended beyond that period the units would be replaced with fresh ones.

One of the major factors contributing to adhesion degradation is the low moisture tolerance that such adhesives have. Moisture entrapped by the attachment ring weakens and eventually destroys the bond between the adhesive material and the skin.

It is therefore an object of the present invention to provide a novel medical electrode unit which has improved adhesion characteristics. Another objective is the provision of such an electrode which is simple and inexpensive yet one which is less subject to deleterious results on adhesion of perspiration and other moisture. Other objects, advantages and details of the novel and improved medical electrode unit provided by this invention appear in the following detailed description of preferred embodiments of the invention and accompanying drawings.

Briefly, a medical electrode unit made in accordance with the invention comprises a dielectric body formed with a cavity therein. A sensing electrode element and a foam pad are mounted in the cavity with the foam pad saturated with electrolyte material. A piece of flexible material having a layer of pressure sensitive adhesive material on a surface thereof is secured to the body and a moisture impermeable protective cover is releasably secured to the adhesive layer so that it protects both the adhesive layer and the foam pad. The piece of flexible material is provided with a plurality of slits which extend between inner and outer unslit or continuous portions surrounding the dielectric body. The slits may be straight or curved and may have several different orientations.

In the accompanying drawings, in which several preferred embodiments of the invention are illustrated:

Figure 1:
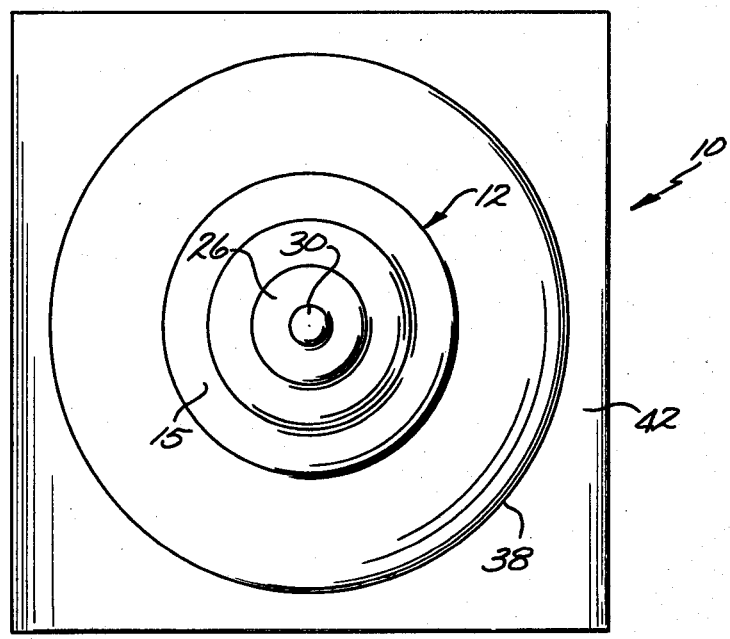
FIG. 1 is a top plan view of a conventional medical electrode unit including a protective cover.

Dimensions of certain of the parts as shown in the drawings may have been modified or exaggerated for purpose of clarity of illustration.

Figure 2:
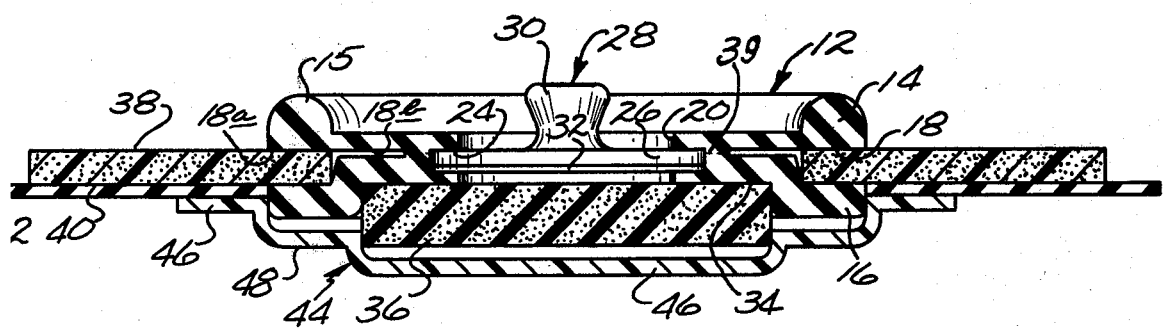
FIG. 2 is a cross sectional elevational view of the FIG. 1 unit.

With reference to FIGS. 1 and 2 a medical electrode unit 10 comprises a generally cylindrical disc like body 12 of dielectric material such as polystyrene having a top cap portion 14 and a bottom base portion 16 separated from one another by an annular groove 18 formed in the outer periphery of body 12. Body 12 is provided with a centrally located bore or cavity 20 extending through the body from the cap to the base. A groove 24 is formed in body 12 in communication with bore 20 and captures therein the outer peripheral flange 26 of electrode member 28. Electrode member 28 can be formed of any suitable material, such as acrylonitrile-butadiene-styrene (ABS resin) which is plated with electrically conductive material, such as silver. Alternatively, the electrode member could be formed of a metallic material such as brass, plated with nickel and overplated with highly electrically conductive material such as silver. The plated plastic version has the advantage of having excellent non corrosion characteristics as well as being relatively inexpensive. Member 28 is formed with a knob portion 30 projecting from flange 26 to facilitate attachments of an electrical lead thereto. Layer 32 is preferably formed of a composite laminate having an inner layer of fine silver or of a relatively hard alloy of high silver content metallurgically bonded to an outer layer of silver chloride, the composite layer 32 being welded or otherwise secured in electrically conductive relation to electrode member 28.

A recess 34 is formed in base 16 in communication with bore 20 forming a seat for a foam pad 36. Pad 36 may be formed of a suitable porous or open-celled material such as urethane foam and is attached to base 16 in any convenient manner, as by heat fusing portions of the foam pad to the seat portion of base 16. A selected quantity of a suitable electrolyte gel which will provide skin contact and form a fluid column from the skin to the sensing electrode without contaminating the adhesive surface of an attachment member 38 saturates foam pad 36. Attachment member 38 is a generally circular shaped foam ring received in groove 18 which projects from body 12 to form a radially extending attachment flange. In assembling the unit top cap 14 and bottom base 16 can be provided as separate elements. Foam ring 38 can then be readily placed on base 16 with cap 14 placed thereover and ultrasonically welded to base 16, as indicated by the dashed lines 39 in FIG. 2, to capture ring 38 therebetween. Ring 38 is formed of flexible material, such as closed-cell polyethylene foam and is provided with a layer of adhesive on a face 40 thereof. A piece of protective material 42, such as a piece of paper coated to render it impervious to moisture and to act as a release agent, cooperates with a cover 44 and is disposed on face 40 of ring 38 with cover 44 extending over the bottom of base 16 and foam pad 36. Cover 44 comprises a flange 46 which is secured to the bottom of paper 42 as by a suitable adhesive and a recessed central plate portion 46 spaced from pad 36 a selected distance joined to flange 46 by an intermediate flange 48.

Groove 18 has a first relatively wide portion 18a which serves as a seat for foam ring 38 and a second narrow portion 18b which provides a spring bias for firmly holding ring 38 in place. Cap 14 has a circular rib 15 which acts as a structural support so that suitable holding force can be transferred to ring 38.

Figure 3:
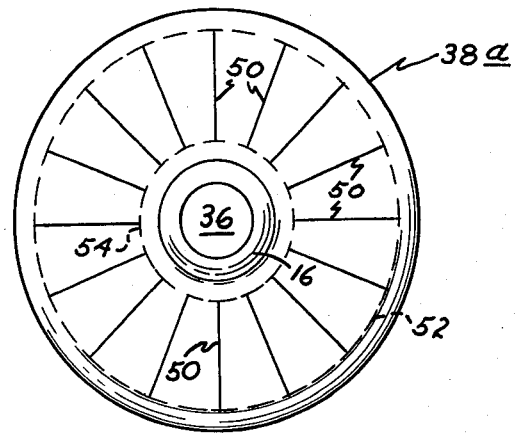
FIG. 3 is a bottom plan view of a unit similar to FIG. 1 but having radially extending slits formed in the foam ring used to adhere the unit to a patient.

With particular reference to FIGS. 3-6 several embodiments are shown looking at the bottom of a unit similar to unit 10 of FIGS. 1 and 2 but with the protective paper 42 and cover 44 removed and with ventilation means formed in the foam ring. In FIG. 3 a series of slits 50 are formed in ring 38a extending entirely through the ring and adhesive layer from bottom face 40 to the top surface. The slits extend a selected distance from the outer periphery of the ring, as denoted by dashed line 52 to a selected distance from base 16, as denoted by dashed line 54. Slits 50 extend radially from the center of ring 38a. The particular number of slits is a matter of choice as long as there are no large portions of the ring which are not ventilated. It is preferred, although not essential that the slits are uniformly spaced about the periphery of the ring. Thus any entrapped air or moisture is allowed to vent from the patient's skin without inteferring with the integrity of the adhesion between adjacent areas of ring 38a.

Figure 4:
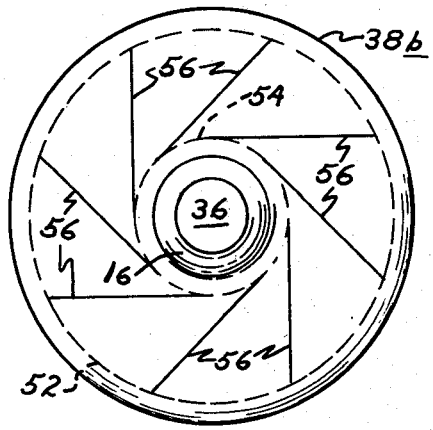
FIGS. 4-6 are views similar to FIG. 3 of other embodiments in which the slits have different configurations and orientations.
Figure 5:
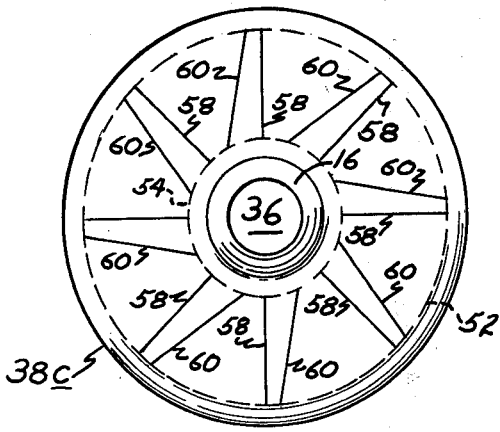

FIG. 4 shows a series of slits 56 extending in directions tangent to circle 54. In FIG. 5 slits 58 and 60 form pairs of slits in which one of each pair is tangent to a circle concentric with circle 54 while the other slit of each pair extends radially from the center of ring 38c.

Figure 6:
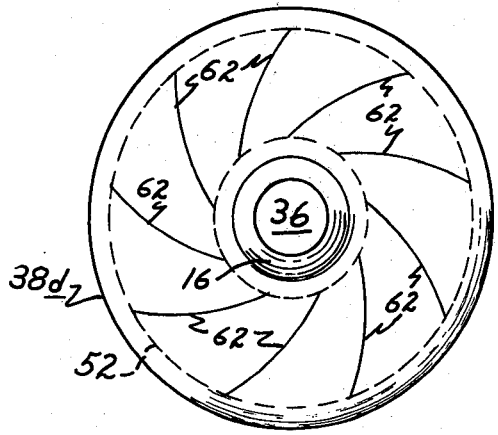

In FIG. 6 slits 62 have a curved configuration. In all cases, it will be noted there are inner and outer rims of rings 38a–38d which are not slitted to ensure that the ribbons formed by adjacent slits do not become entangled with one another and that sufficient force is transmitted to the central hub portion of unit 10 so that the sensing portion is in good sensing contact with the patient's skin.

In order to provide relatively long shelf life the units are preferably placed in hermetically sealed foil pouches until ready for use.

In addition to improved ventilation provided by the slits in attachment flange 38 which allows body fluids to escape from under the medical electrode unit thereby preventing the fluids from degrading the adhesion and hence the integrity of the bond several other advantages are obtained by using the slits. That is, the slits also reduce the formation of air pockets which whould otherwise adversely affect the bond between the unit and the patient's skin. Additionally, it may be noted that in the event that any of the gel electrolyte is forced out of its cavity its contact with the adhesive layer of flange 38 will be minimized since it can escape through the slits. The slits also render the attachment flange more flexible allowing it to conform to body contours more easily and with less adhesive force needed to maintain flange 38 in the conformed configuration. The inner rim of flange 38 which is not slitted ensures optimum electrode contact with the skin while allowing ventilation over the major portion of the flange. The degree of this ventilation can be varied, particularly in the FIGS. 4 and 6 embodiments, if desired, by a slight twisting motion when the units are first applied to the body to cause the slits to open up to a selected extent. This slight twisting motion also has the advantage of severing any portions of the adhesive layer in the event that such have recoalesced across the slits.

Although the present invention has been shown and described in terms of specific preferred embodiments, it will be apparent that changes and modifications are possible without departing from the spirit and scope of the invention as defined in the appended claims.

We claim:

1. A medical electrode unit comprising a dielectric body having a cavity therein which is open at one end, a conductive electrode element mounted on the body, the electrode element having a surface disposed in the cavity, the electrode element having means for permitting electrical connection to be made to the electrode element, a resilient, foam pad having pores extending therethrough secured to the body within the cavity, the foam pad having a surface extending adjacent the open cavity end, a selected quantity of electrolyte gel disposed in the cavity and saturating the foam pad and means for securing the dielectric body to a patient including a flexible ring secured around the periphery of the body in surrounding relation to the open cavity end, the ring having a top and bottom surface, the bottom surface being adjacent the open cavity end, an adhesive layer provided on the bottom surface and a plurality of slits formed in the ring extending from the top to the bottom surface, each slit extending continuously between an outer annular portion of the ring adjacent the outer periphery of the ring and an inner annular portion of the ring adjacent the outer periphery of the body.

2. A medical electrode unit according to claim 1 in which the ring is formed of foam material.

3. A medical electrode unit according to claim 1 in which the ring is generally circular and the slits extend in the direction of radii of the circle.

4. A medical electrode unit according to claim 3 in which other of said slits are tangent to a circle concentric with the ring.

5. A medical electrode unit according to claim 1 in which the ring is circular and the slits are tangent to a circle concentric with the ring.

6. A medical electrode unit according to claim 1 in which the slits are curved in length.

7. A medical electrode unit according to claim 1 including a protective cover releasably attached to the adhesive layer on the bottom surface of the ring.

8. A medical electrode unit comprising a dielectric body generally cylindrical in shape having a top cap portion and a bottom base portion separated from each other by a groove extending around the circumference of the body, a bore extending through the body from a top surface to a bottom surface of the body, an electrically conductive element mounted on the body and disposed in the bore, means on the conductive element to facilitate attachment to an electrical lead, an open celled foam pad mounted in the base portion of the body and disposed in the bore with a surface of the pad adjacent the bottom surface of the body, an electrolyte gel saturating the foam pad, a ring of flexible material received in the groove and extending radially outwardly from the cylindrical shaped body, the ring having a top and bottom surface, the bottom surface of the ring being adjacent the bottom surface of the body, the bottom surface of the ring covered with an adhesive layer to facilitate attachment of the dielectric body to the skin of a patient, and a plurality of slits formed through the ring from the bottom surface to the top surface, the ring formed with continuous inner and outer marginal portions with the slits generally evenly spaced about the ring, each slit extending continuously between the inner and outer marginal portions.

* * * * *